(12) United States Patent
Shelley et al.

(10) Patent No.: US 12,040,058 B2
(45) Date of Patent: Jul. 16, 2024

(54) SYSTEMS AND METHODS FOR PROVIDING CLINICAL TRIAL STATUS INFORMATION FOR PATIENTS

(71) Applicant: Flatiron Health, Inc., New York, NY (US)

(72) Inventors: Addison Shelley, New York, NY (US); Achin Batra, Jersey City, NJ (US); Alexander Padmos, New York, NY (US); Angel Leung, Brooklyn, NY (US); Dominic Green, Brooklyn, NY (US); Frank Zexi Chen, Forest Hills, NY (US); Harvey James Hamrick, Jr., Atlanta, GA (US); Janet Donegan, Park City, UT (US); Jessie Tseng, Brooklyn, NY (US); Lauren Sutton, New York, NY (US); Nathan Chan, New York, NY (US); Rahul Bafna, New York, NY (US); David Light, San Francisco, CA (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 16/745,618

(22) Filed: Jan. 17, 2020

(65) Prior Publication Data
US 2020/0234802 A1    Jul. 23, 2020

Related U.S. Application Data

(60) Provisional application No. 62/816,558, filed on Mar. 11, 2019, provisional application No. 62/793,600, filed on Jan. 17, 2019.

(51) Int. Cl.
*G16H 10/20* (2018.01)
*G16H 10/60* (2018.01)
(Continued)

(52) U.S. Cl.
CPC .............. *G16H 10/20* (2018.01); *G16H 10/60* (2018.01); *G16H 15/00* (2018.01); *G06F 3/0482* (2013.01)

(58) Field of Classification Search
CPC ........ G16H 10/20; G16H 15/00; G16H 10/60; G06F 3/0482
See application file for complete search history.

(56) References Cited

U.S. PATENT DOCUMENTS 10,971,272 B1 * 4/2021 Nair ...................... G06F 3/0482
2005/0261940 A1 * 11/2005 Gay ...................... G16H 40/20
705/28

(Continued)

*Primary Examiner* — Robert W Morgan
*Assistant Examiner* — Liza Tony Kanaan
(74) *Attorney, Agent, or Firm* — FINNEGAN, HENDERSON, FARABOW, GARRETT & DUNNER, LLP

(57) ABSTRACT

A graphical user interface for displaying an electronic medical record associated with a patient is provided. The graphical user interface may include an area configured to display patient information, which may include at least a name of the patient. The graphical user interface may also include an indicator displayed in association with the name of the patient. The indicator may include information specifying that the patient is potentially eligible for one or more trials, the patient is participating in one or more trials, or the patient has completed one or more trials.

19 Claims, 23 Drawing Sheets

(51) Int. Cl.
  *G16H 15/00*  (2018.01)
  *G06F 3/0482*  (2013.01)

(56) References Cited

U.S. PATENT DOCUMENTS

| | | | | |
|---|---|---|---|---|
| 2010/0003689 | A1* | 1/2010 | Hoon | C12Q 1/6886 |
| | | | | 435/6.14 |
| 2010/0008975 | A1* | 1/2010 | Amler | G01N 33/57423 |
| | | | | 424/139.1 |
| 2013/0218594 | A1* | 8/2013 | Skocic | G06Q 10/10 |
| | | | | 705/3 |
| 2013/0332191 | A1* | 12/2013 | Hoffman | G06Q 30/02 |
| | | | | 705/3 |
| 2016/0070859 | A1* | 3/2016 | Ignatenko | G16B 50/40 |
| | | | | 707/693 |
| 2016/0110523 | A1* | 4/2016 | Francois | G16H 10/20 |
| | | | | 705/2 |
| 2016/0147953 | A1* | 5/2016 | Menon | G16H 10/20 |
| | | | | 705/3 |
| 2017/0228501 | A1* | 8/2017 | Turner, Jr. | G06Q 30/0277 |
| 2018/0046780 | A1* | 2/2018 | Graiver | G06F 40/44 |

\* cited by examiner

| | | | | Add clinical trial |
|---|---|---|---|---|
| Filter by name | All trial statuses ▸ | Select diseases... ▸ | All lines of therapy ▸ | |
| Filtered by: None. | | | | Showing 20 of 20 rows |

| Trial name ▴ | Trial description | Status | Disease | Line of therapy | |
|---|---|---|---|---|---|
| Trial A | Trial A Description | Active, Not Recruiting | Breast Cancer | Metastatic: 1st line<br>Metastatic: 2nd line | ... |
| Trial B | Trial B Description | Closed | Prostate Cancer | None selected | ... |
| Trial C | Trial C Description | Active, Recruiting | Non-Small Cell Lun... | Adjuvant | ... |
| Trial D | Trial D Description | Pending | Breast Cancer | Metastatic: 1st line | ... |
| Trial E | Trial E Description | Active, Recruiting | Colon Cancer | Metastatic: 1st line | ... |
| Trial F | Trial F Description | Active, Recruiting | Colon Cancer<br>Rectal Cancer | Metastatic: 3rd line and beyond | ... |
| Trial G | Trial G Description | Pending | Breast Cancer | Metastatic: 1st line<br>Metastatic: 2nd line | ... |
| Trial H | Trial H Description | Pending | Ovarian Cancer<br>Ovarian, Epithelial C...<br>Ovarian, Malignant ...<br>... and 1 others | Metastatic: 2nd line | ... |

Add a New Clinical Trial

Protocol Overview

Study ID

Enter the NCT identifier to retrieve the protocol overview from clinicaltrials.gov.

NCT Identifier

| NCT0123456 | Retrieve Trial Information |

☐ NCT identifier not available

Trial Name *

| Trial A |

Study Drug

| Drug X |

Sponsor

| Sponsor1 |

Study Type

| Interventional |

Trial Description *

| Standard of care + Drug X in BRCA Mutant Breast Cancer |

Contract Research Organization

|  |

*FIG. 3*

Suggested trials Show description

Fri., 11/08/2018 | < | > | All physicians ▼ | All locations ▼ | Hide viewed appointments | Print Filtered by: None.

| Patient | Diagnosis | Visit Type | Physician | Location | Current status on trial(s) | |
|---|---|---|---|---|---|---|
| ⊚ Genelle Larson A056176 | Breast Cancer | Office Visit | Klocko, Dagmar | South Aletha Canc... | Trial A<br>Trial B | ○ In Pre-screening<br>○ Deemed ineligible |
| ⊚ Ollie X. Stiedemann A023608 | Breast Cancer and 7 others | Office Visit | Barrows, Aurelia | Cancer Specialists... | Trial B<br>Trial C<br>Trial D | ○ Watching<br>○ In Pre-screening<br>○ Deemed ineligible |
| ⊚ Christina Weissnat A050336 | Breast Cancer and 3 others | Treatment | | Kellview Cancer S... | Trial C<br>Trial E<br>Trial B | ⊙ Active<br>○ In Consenting Pr...<br>○ Deemed ineligible |

*FIG. 7*

Suggested trials

Fri., 11/08/2018

Filtered by: None.

| Patient | |
|---|---|
| ⊘ Genelle Larson A056174 | |
| ⊘ Ollie X. Stiedemann A023408 | |
| ⊘ Christina Weissna A050334 | |

---

Ollie X. Stiedemann   DOB: 08/25/1969 (50 years old)   Set reminder | Mark unviewed | Close

Notifications:

10/22/2018: Consider this patient, from L zAltos-Sutton in OncoEMR — 821

Patient Clinical Info   [Open OncoEMR Documents]

Diagnosis

Primary Diagnosis in OncoEMR

Breast Cancer                                           11/16/2017
Stage IIIA (11/16/2017)                         Date of diagnosis

Disease Status

Breast model                                    Highly Likely
Metastatic Disease                   last updated: 09/22/2017

Trials — 822

Trial B pending
○ Watching

Breast Cancer   ⊘
HER2 pos        ⊘
HR pos          ⊘
Metastatic      ⊘

Trial C
active, not recruiting
○ In Pre-screening

*FIG. 8A*

Suggested trials

Fri, 11/08/2018

Filtered by: None.

| Patient | |
|---|---|
| ⊘ Genelle Larson A056174 | |
| ⊘ Ollie X. Stiedemann A023408 | |
| ⊘ Christina Weissna A050334 | |

---

Ollie X. Stiedemann  DOB: 08/25/1969 (50 years old)  [Set reminder] [Mark unviewed] [Close]

Notifications:

10/22/2018: Consider this patient, from L zAltos-Sutton in OncoEMR — Sutton

Patient Clinical Info  [Open OncoEMR Documents]

Diagnosis

Primary Diagnosis in OncoEMR                                11/16/2017
Breast Cancer                                               Date of diagnosis
Stage IIIA (11/16/2017)

Disease Status                                          Highly Likely
                                                            last updated: 09/22/2018

Breast model
Metastatic Disease

Trials > Trial B

Trial Timeline

10/28/2018  ○  Watching by svorona

10/18/2018  ○  In Consenting Process by cnightingale

08/21/2017  ○  Considered by N zAltos-Chan

07/05/2017  ○  In Pre-screening by lsutton

*FIG. 8B*

Patient Clinical Info    Open in OncoEMR

Diagnoses:

Essential (primary) hypertension    01/21/14

Colon Cancer
Stage III (10/05/16)    11/04/11

Biomarkers

MSI    02/15/2017: High
NRAS    02/15/2017: Negative
KRAS    02/15/2017: Positive

Drug order History:

Cyclophosphamide    First Order: 02/01/2017
Doxorubicin    First Order: 03/01/2017

---

Trials > Trial B > Add Status    Done

Trial B

○ In Pre-screening
When did you begin pre-screening the patient?*

October 2016

| S | M | T | W | T | F | S |
|---|---|---|---|---|---|---|
|   |   |   |   |   |   | 1 | 2 | 3 | 4 |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |
| 26 | 27 | 28 | 29 | 30 | 31 |

Comment to providers will be surfaced in OncoEMR.

Patient has no previous history of heart disease.
Patient meets the inclusion criteria of the trial, including gender & age.

*FIG. 10*

Clara Smith

Room: Exam Room 1 ▾
MEMO:

( ON STUDY ) ( POTENTIAL TRIALS (2) ) ( IN FOLLOW UP )

Treatment plan

| < > | Tue 08/20/2015 | Thurs 09/11/2015 | Mon 09/14/2015 | Today 09/20/2015 | Fri 09/22/2015 | Tue 09/27/2015 |
|---|---|---|---|---|---|---|
| General | | | | | | |
| Change History | | | | | | |
| mFolfox 6 Bevacuzumab | 1:1 | 1:8 | 2:1 | 2:3 | 2:8 | 3:1 |
| Zantac PO | | | 150mg | | | 150mg |
| OXALIplatin IV | | | 85mg | | | 85mg |
| Leucovorin Calcium IV | | | 704mg | | | 704mg |
| Bevacizumab (Avastin IV) | | | 304mg | | | 304mg |
| CBC | | • | • | | • | • |
| CMP | | | • | | | • |

Clara Smith

Room: Exam Room 1 ▼

1110 — ON STUDY    1131 — POTENTIAL TRIALS (2)    1132

Potential trials (2) — 1142

| Trial name | Coordinator | | Physician Action |
|---|---|---|---|
| Trial B | Sutton Lauren  5/5/18  Patient has no previous history of heart disease. Patient meets the inclusion criteria of the trial, including gender & age. | | Do not consider    Consider |
| Trial C | Sutton, Lauren  5/14/18 | | Do not consider    Consider |

Treatment

∧
∨

General
Change History
mFolfox 6 Bev
Zantac PO

| | | | | |
|---|---|---|---|---|
| OXALIplatin IV | | 85mg | | 85mg |
| Leucovorin Calcium IV | | 704mg | | 704mg |
| Bevacizumab (Avastin IV) | | 304mg | | 304mg |
| CBC | • | • | • | • |
| CMP | | • | | • |

Clara Smith

Room: Exam Room 1 ▼

ON STUDY — Marked patient as 'Do not Consider' for Trial B   Undo   Close — 1131, 1142, 1152

1110

Please provide a reason (optional)

☐ This patient does not want to be on a clinical trial
☐ This patent has poor performance status
☐ Treatment not indicated
☐ Other

[Please provide a reason]

[Cancel] [Save]

Treatment

Change History

| General | 1:1 | 1:8 | 2:1 | 2:3 | 2:8 | 3:1 |
|---|---|---|---|---|---|---|
| mFolfox 6 Bevacuzumab | | | | | | |
| Zantac PO | | | 150mg | | | 150mg |
| OXALIplatin IV | | | 85mg | | | 85mg |
| Leucovorin Calcium IV | | | 704mg | | | 704mg |
| Bevacizumab (Avastin IV) | | | 304mg | | | 304mg |
| CBC | | • | • | | • | • |
| CMP | | | • | | | • |

Notification & reminders

My notifications ▼

Current

| Date | Patient | Content | Details | |
|---|---|---|---|---|
| 01/14/2018 | Clara Smith 123456 | Trial B: Do not consider this patient, from Smith, Jeff in OncoEMR *patients have moved.* | Set on 09/14/2-18 | Delete |
| 09/14/2018 | Clara Smith 123456 | Trial C: Consider this patient, from Smith, Jeff in OncoEMR | Set on 09/14/2-18 | Delete |

*FIG. 12*

Visit schedule   Show description

Wed. 07/01/18  [▼]

Search by name or MRN  [🔍]  [∨]

Filtered by: None
☐ Wed, 07/01/18

| All physicians ▼ | All diagnoses ▼ | All locations ▼ | Hide viewed appointments |
| All visit types ▼ | All trials ▼ | All statuses ▼ | Print |

| Patient | Diagnosis | Visit Type | | Physician | Location | Current Status on trial(s) | |
|---|---|---|---|---|---|---|---|
| ⊚ Julie Clark 88885 | Breast Cancer | Treatment | 9:15 am | Hill, Leo | Cancer Center of ... | Trial A<br>Trial B<br>Trial C<br>Trial D | ● Active<br>○ Watching<br>○ Watching<br>○ Deemed ineligible |
| ⊚ Elnora Lee 94375 | Soft Tissue Sarcoma | Treatment | 9:15 am | Hill, Leo | Cancer Center of ... | Trial A | ○ Candidate |
| ⊚ Tula Simpsons 34232 | Breast Cancer | Treatment | 9:15 am | Hill, Leo | Cancer Center of ... | Trial E<br>Trial F<br>Trial G<br>Trial D | ○ Candidate<br>○ Watching<br>○ Watching<br>○ Deemed ineligible |

Visit schedule    Show description

Wed. 07/01/18  [<] [>]

[All physicians ▼]  [All locations ▼]  [Hide viewed appointments]  [Print]

Search by name or MRN  [🔍]  [All diagnoses ▼]  [All visit types ▼]  [All trials ▼]  [ⓘ]

Filtered by: None
☐ Wed, 07/01/18    [All statuses ▼]

| Patient | Diagnosis | Visit Type | | Physician | Location | Current Status on Sponsor1 | |
|---|---|---|---|---|---|---|---|
| ⊙ Julie Clark 88885 | Breast Cancer | Treatment | 9:15 am | Hill, Leo | Cancer Center of ... | Trial A<br>Trial B<br>Trial C<br>Trial D | ● Active<br>○ Watching<br>○ Watching<br>○ Deemed ineligible |
| ⊙ Tula Simpsons 34232 | Breast Cancer | Treatment | 9:15 am | Hill, Leo | Cancer Center of ... | Trial E<br>Trial F<br>Trial G<br>Trial D | ○ Candidate<br>○ Watching<br>○ Watching<br>○ Deemed ineligible |

Visit schedule    Show description

Wed. 07/01/18  [▼] [▲] | All physicians ▼ | All locations ▼ | Hide viewed appointments | Print Search by name or MRN  [🔍] | All diagnoses ▼ | All visit types ▼ | All trials ▼ | All statuses ▼ | ⓘ

Filtered by: None
☐ Wed, 07/01/18

| Patient | Diagnosis | Visit Type | | Physician | Location | Current Status on Sponsor2 | |
|---|---|---|---|---|---|---|---|
| ⊙ Julie Clark 88885 | Breast Cancer | Treatment | 9:15 am | Hil, Leo | Cancer Center of ... | Trial A<br>Trial B<br>Trial C<br>Trial D | ● Active<br>○ Watching<br>○ Watching<br>○ Deemed ineligible |
| ⊙ Elnora Lee 94375 | Soft Tissue Sarcoma | Treatment | 9:15 am | Hil, Leo | Cancer Center of ... | Trial A | ○ Candidate |

*FIG. 13C*

SYSTEMS AND METHODS FOR PROVIDING CLINICAL TRIAL STATUS INFORMATION FOR PATIENTS

CROSS-REFERENCES TO RELATED APPLICATIONS

This application claims the benefit of priority of U.S. Provisional Patent Application No. 62/793,600, filed Jan. 17, 2019, and U.S. Provisional Patent Application No. 62/816,558, filed Mar. 11, 2019, all of which are incorporated herein by reference in their entirety.

BACKGROUND

Technical Field

The present disclosure relates to systems and methods for providing status information for a patient and one or more clinical trials.

Background Information

Identifying patients who are eligible for clinical trials is one of the challenges the cancer research community faces. While there are reasons that may dissuade a patient from participating in clinical trials, there are also many barriers. For example, identifying a patient at just the right time such as, for instance, when they are ready to be put on a therapy but have not yet started one, is often challenging when a practice may have dozens of trials open, each with a dozen or more inclusion/exclusion criteria, and with hundreds of patients coming into a practice a day. Thus, to overcome these challenges faced by existing systems, it is desirable to identify eligible patients for a clinical trial and eligible trials for a patient more efficiently. Additionally, it is desirable to identify the patients scheduled for an office visit who may be eligible for trials to improve trial recruitment, which may benefit both patients and researchers. Moreover, it is desirable to provide research coordinators and/or health care service providers an improved graphical user interface for displaying information relating to a patient and one or more trials for which the patient is potentially eligible. Further, it is desirable to provide systems and methods with improved workflows between research coordinators and health care service providers by automatically sharing updated trial information among them, which may significantly increase the number of patients participating in clinical trials and benefit both patients and the medical study community.

SUMMARY

Embodiments consistent with the present disclosure include systems and methods for providing information related to a patient and one or more clinical trials. The information related to the patient may include status information for the patient and one or more clinical trials.

In one embodiment, a graphical user interface may display an electronic medical record associated with a patient. The graphical user interface may include an area configured to display patient information, which may include at least a name of the patient. The graphical user interface may also include an indicator displayed in association with the name of the patient. The indicator may include information specifying that the patient is potentially eligible for one or more trials, the patient is participating in one or more trials, or the patient has completed one or more trials.

In one embodiment, an apparatus may comprise at least one processor configured to display a graphical user interface. The graphical user interface may include an area configured to display patient information associated with a patient, which may include at least a name of the patient. The graphical user interface may also include an indicator displayed in association with the name of the patient. The indicator may include information specifying that the patient is potentially eligible for one or more trials, the patient is participating in one or more trials, or the patient has completed one or more trials.

In one embodiment, a computer-implemented system may manage electronic medical records. The system may include at least one processor configured to receive information indicating that a patient is potentially eligible for a trial, and update an electronic medical record of the patient based on the received information. The at least one processor may also be configured to provide, to a first user, a first user interface, which may include an indicator indicating that the patient is potentially eligible for the trial. The at least one processor may further be configured to receive, from the first user via the first user interface, input for updating trial information associated with the trial and the patient. The updated trial information may include information indicating whether the patient is being considered for participation in the trial. The at least one processor may also be configured to provide, to a second user, a second user interface, which may include at least portion of the updated trial information associated with the trial and the patient.

In one embodiment, a computer-implemented method may manage electronic medical records. The method may include receiving information indicating that a patient is potentially eligible for a trial, and updating an electronic medical record of the patient based on the received information. The method may also include providing, to a first user, a first user interface. The first user interface may include an indicator indicating that the patient is potentially eligible for the trial. The method may further include receiving, from the first user via the first user interface, input for updating trial information associated with the trial and the patient. The updated trial information may include information indicating whether the patient is being considered for participation in the trial. The method may also include providing, to a second user, a second user interface, which may include at least portion of the updated trial information associated with the trial and the patient.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 2 is a diagram illustrating an exemplary graphical user interface for viewing trials, consistent with the present disclosure.

FIG. 3 is a diagram illustrating an exemplary graphical user interface for receiving user input for creating a new trial, consistent with the present disclosure.

FIG. 7 is a diagram illustrating an exemplary graphical user interface for providing one or more suggested trials for patients, consistent with the present disclosure.

FIGS. 8A and 8B are diagrams illustrating an exemplary graphical user interface for providing information of a patient and suggested trials, consistent with the present disclosure.

FIG. 10 is a diagram illustrating an exemplary graphical user interface for displaying and modifying trial information for a patient, consistent with the present disclosure.

FIGS. 11A-11F are diagrams illustrating exemplary graphical user interfaces for displaying and modifying trial information for a patient, consistent with the present disclosure.

FIG. 12 is a diagram illustrating an exemplary graphical user interface for displaying one or more notifications relating to updates on trial information of a patient, consistent with the present disclosure.

FIGS. 13A-13C are diagrams illustrating exemplary graphical user interfaces for displaying one or more trials, consistent with the present disclosure.

DETAILED DESCRIPTION

Figure 1A:
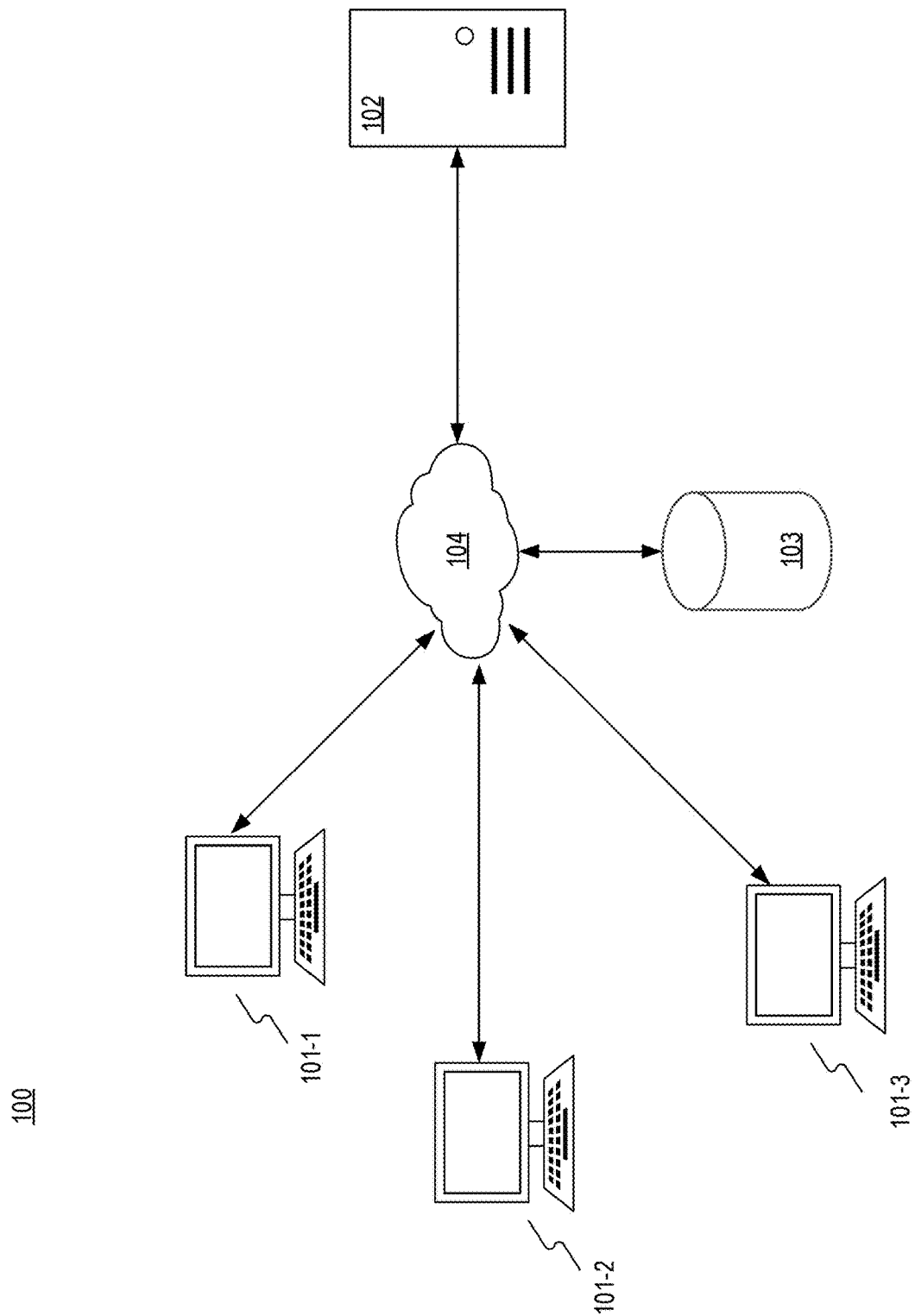
FIG. 1A is a block diagram illustrating an exemplary system for providing one or more suggested patients for a trial, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, non-volatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

In this disclosure, a system may provide a graphical user interface to display an electronic medical record associated with a patient. According to one embodiment, the system may provide a graphical user interface including an area configured to display patient information, the patient information including at least a name of the patient. The graphical user interface may also include an indicator displayed in association with the name of the patient, and the indicator may include information specifying that the patient is potentially eligible for one or more trials, the patient is participating in one or more trials, or the patient has completed one or more trials. Potential benefits for using the disclosed systems and methods may include enabling users to view a patient's clinical trial status easily. For example, physicians may be able to easily identify trial treatment options for their patients. As another example, research coordinators or patient schedulers may be able to readily determine whether or not a patient is enrolled on a study, which may provide more flexibility when scheduling patient visits.

FIG. 1A illustrates an exemplary system 100 for implementing embodiments consistent with the present disclosure, described in detail below. As shown in FIG. 1A, system 100 may include one or more client devices 101, a computing device 102, a database 103, and a network 104. It will be appreciated from this disclosure that the number and arrangement of these components are exemplary and provided for purposes of illustration. Other arrangements and numbers of components may be used without departing from the teachings and embodiments of the present disclosure.

A client device 101 (e.g., client device 101-1, 101-2, 101-3) may be configured to receive user input from a user for creating a new trial. For example, client device 101 may reside at a clinic, and a user (e.g., a physician or administrator) may enter information for creating a new trial portfolio at an input device of client device 101. By way of example, the user may enter an identification number (e.g., a National Clinical Trial (NCT) number or ClinicalTrials.gov identifier) at an interface of client device 101 for creating a new trial, and client device 101 may transmit the identification number to computing device 102. Computing device 102 may create a trial portfolio for the new trial based on the identification number. Client device 101 may also receive and present information received from computing device 102. For example, client device 101 may receive information relating to suggested patients for one or more trials from computing device 102 and present the information at an interface of client device 101 to the user. In some embodiments, client devices 101-1, 101-2, and 101-2 may reside at the same site or different sites.

Computing device 102 may be configured to receive information from client device 101 for creating the new trial portfolio from client device 101. Computing device 102 may also create a trial portfolio based on the information received from computing device 102. For example, computing device 102 may receive an NCT number from client device 101 and obtain information relating to the NCT number from a database, which may be an external database (e.g., database 103) or an internal database (e.g., database 160 illustrated in FIG. 1B). The trial information received by computing device 102 may include at least a portion of trial eligibility criteria associated with the trial. Computing device 102 may also create a new trial portfolio for the trial based on the trial information. The trial portfolio may include one or more trial eligibility criteria for determining whether a patient is eligible for the trial. For example, the trial eligibility criteria may include an age restriction that an eligible patient must be over 18 years old. Computing device 102 may further automatically generate an algorithm for suggesting one or more eligible patients for the new trial based on the trial eligibility criteria. For example, computing device 102 may automatically generate an algorithm representing an expression tree (e.g., expression tree structures 401, 402 illustrated in FIGS. 4A and 4B) based on the trial eligibility criteria, and the nodes and/or leaves of the expression tree may represent the trial eligibility criteria.

Computing device 102 may also be configured to obtain electronic medical records associated with a plurality of patients and determine whether one or more patients may be eligible for the new trial based on the algorithm and electronic medical records. For example, computing device 102 may obtain electronic medical records associated with the patients of a clinical (e.g., the clinical associated with client device 101). Computing device 102 may determine one or more patients among the patients of the clinical who may be eligible for the new trial based on the algorithm and electronic medical records. By way of example, computing device 102 may create a namedtuple that has numbers and a series of letters for each of the patients based on the electronic medical record (e.g., age, disease, biomarkers). Computing device 102 may evaluate the created namedtuples associated with the patients against the expression tree, which may return a number indicating the eligibility for each of the patients. For example, the expression-tree algorithm may output "0" for ineligible or "1" for eligible. Alternatively, the algorithm may output a probability value indicating the eligibility for each of the patients.

Computing device 102 may further be configured to output one or more suggested eligible patients for the new trial. For example, computing device 102 may output one or more suggested patients to an output device (e.g., a display, printer). Alternatively or additionally, computing device 102 may transmit instructions for displaying information representing the one or more suggested patients to client device 101, which may present the information to the user.

In some embodiments, computing device 102 may be configured to provide one or more suggested trials for a patient. For example, the user may select a patient via the input device of client device 101 (or computing device 102), and computing device 102 may provide one or more trials for which the patient may be eligible based on one or more patient-trial matching algorithms and the electronic medical record associated with the patient.

In some embodiments, client device 101 and computing device 102 may be integrated into one device configured to perform the functions of client device 101 and computing device 102 disclosed in this application. For example, a user may input information for creating a new trial via input device 153 of computing device 102, which may display one or more suggested patients for the new trial via an output device (e.g., output device 154, discussed below).

Database 103 may be configured to store information and data for one or more components of system 100. For example, database 103 may store electronic medical records associated with one or more patients. Database 103 may also store information relating to one or more trials. For example, database 103 may store trial eligibility criteria associated with each of the trials. In some embodiments, database 103 may also store patient-trial matching algorithms for determining one or more suggested eligible patients for a trial, and/or one or more suggested eligible trials for a patient. Client device 101 and/or computing device 102 may be configured to access and obtain the data stored on database 103 via network 104. In some embodiments, database 103 may be operated by a third party. For example, computing device 102 may request information relating to a particular trial from database 103, which may transmit the requested information to computing device 102. By way of example, computing device 102 may request the information of trial by transmitting a trial identifier (e.g., an NCT number) to database 103, which may transmit the requested information (e.g., trial eligibility criteria) to computing device 102.

Network 104 may be configured to facilitate communications among the components of system 100. Network 104 may include a local area network (LAN), a wide area network (WAN), portions of the Internet, an Intranet, a cellular network, a short-ranged network (e.g., a Bluetooth™ based network), or the like, or a combination thereof.

Figure 1B:
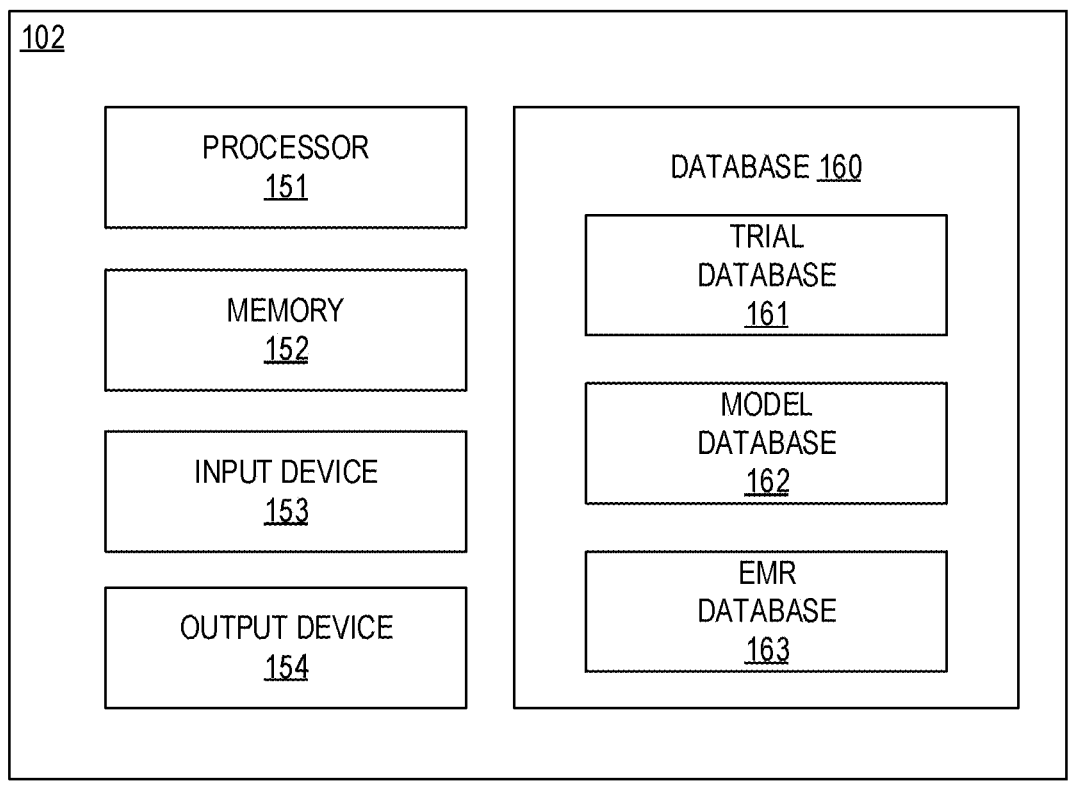
FIG. 1B is a block diagram illustrating an exemplary computing device for providing one or more suggested patients for a trial, consistent with the present disclosure.

FIG. 1B is a block diagram illustrating an exemplary computing device 102. Computing device 102 may include at least one processor (e.g., processor 151), a memory 152, an input device 153, an output device 154, and a database 160.

Processor 151 may be configured to perform one or more functions described in this application. Computing device 102 may also include a memory 152 that may store instructions for various components of computing device 102. For example, memory 152 may store instructions that, when executed by processor 151, may be configured to cause processor 151 to perform one or more functions described herein.

Input device 153 may be configured to receive input from the user of computing device 102, and one or more components of computing device 102 may perform one or more functions in response to the input received. In some embodiments, input device 153 may include an interface displayed on a touchscreen (e.g., output device 154). Output device 154 may be configured to output information and/or data to the user. For example, output device 154 may include a display configured to display one or more suggested patients for a trial. In some embodiments, output device 154 may include a touchscreen.

Database 160 may be configured to store various data and information for one or more components of computing device 102. For example, database 160 may include a trial database 161, a model database 162, and an electronic medical record (EMR) database 163. Trial database 161 may be configured to store information relating to one or more trials. For example, trial database 161 may store a trial portfolio for each of the trials, which may include trial eligibility criteria of a trial. Trial eligibility criteria of a trial may include a trial status, a trial disease, a trial line of therapy, an eligibility age, a trial biomarker criterion, or the like, or a combination thereof. In some embodiments, a trial portfolio may also include trial name, trial description, or the like, or a combination thereof. Trial database 161 may further store edit history including changes made to a trial. Computing device 102 may obtain information relating to the trials from trial database 161 and modify the information if needed. For example, computing device 102 may create a trial portfolio for a new trial and store the trial portfolio into trial database 161.

Model database 162 may store patient-trial matching models or algorithms. A patient-trial matching algorithm refers to an algorithm for determining one or more eligible patients for a trial and/or for determining one or more suggested eligible trials for a patient. Computing device 102 may obtain algorithms from model database 162. In some embodiments, computing device 102 may create an algorithm for a new trial and store the created algorithm into model database 162. EMR database 163 may store electronic medical records associated with patients. Processor 151 may receive one or more electronic medical records from EMR database 163.

FIG. 2 is a diagram illustrating an exemplary graphical user interface 200 for viewing trials, consistent with the present disclosure. User interface 200 may be displayed via output device 154 of computing device 102 (e.g., a display or touchscreen). Alternatively or additionally, computing device 102 may transmit instructions to client device 101 for displaying graphical user interface 200 via an output device of client device 101 (e.g., a display or touchscreen). Computing device 102 may obtain trial data from a database (e.g., database 103, database 160) and render graphical user interface 200 based on the obtained trial data.

User interface 200 may include a trial list 201. Trial list 201 may include trial name, trial description, trial status, trial disease, trial line of therapy, or the like, or a combination thereof. User interface 200 may also include one or more filters 202, such as filters by trial name, trial description, trial status, trial disease, trial line of therapy, or the like, or a combination thereof. In some embodiments, for each trial, graphical user interface 200 may display the edit history, which may include changes made to the trial information by users at the practice. Thus, users may be able to access one location to see all clinical trials across their practice, the trial status, and the disease and line of therapy that the trial is recruiting. This may help users understand where there may be a gap in their trial portfolio and where they may need to open another trial.

User interface 200 may also include a button 203 for adding a new trial. For example, the user may click or select button 203 (e.g., using a data input device or via selection on a touchscreen), and computing device 102 may render another graphical user interface for the user to enter the information relating to the new trial.

FIG. 3 is a diagram illustrating an exemplary graphical user interface 300 for receiving user input for creating a new trial, consistent with the present disclosure. User interface 300 may be displayed via output device 154 of computing device 102 (e.g., a display or touchscreen), and the user may enter information via input device 153. Alternatively or additionally, computing device 102 may transmit instructions to client device 101 for displaying graphical user interface 300 via an output device of client device 101 (e.g., a display or touchscreen) and for receiving user input via an input device of client device 101.

User interface 300 may include one or more fields for the user to enter to add the new trial. For example, the user may enter a trial identification number. Computing device 102 may obtain or generate a trial based on the trial identification number. By way of example, the user may enter an NCT number, and computing device 102 may obtain the trial information from a database or a third party (e.g., clinicaltrials.gov) based on the received NCT number, including, for example, trial name, study drug, sponsor, study type, trial description, diagnosis, biomarker criteria, line of therapy, or the like, or a combination thereof. Computing device 102 may also populate the information obtained in graphical user interface 300 accordingly. In some embodiments, the user may enter at least a portion of the trial information manually. For example, if an NCT number is not available, the user may check a box to indicate such. User interface 300 may prompt the user to manually complete these fields.

In some embodiments, the trial information may include site information identifying a location where the new trial is to be conducted. For example, the user may enter site information that may help medical practices have oversight into the operations at their practice and receive reporting on their trial performance. The operational data fields may include site ID, principal investigator, trial status, enrollment initiation date, enrollment closing date, institutional review board (IRB) approval date, site initiation visit date, contract execution date, number of days for data entry, enrollment goal (e.g., the number of patients), links to external sources, or the like, or a combination thereof.

Computing device 102 may create a trial portfolio for the new trial store the trial information in database 103 and/or database 160. The trial portfolio may include trial eligibility criteria of the trial. A potential benefit of this approach may be that the user of the system (e.g., an administrator, physician, research coordinator) is able to determine eligible patients at the practice (e.g., a clinical site) against the eligibility criteria. Additionally, the system can provide the user with operational reporting on the trials and patients. This approach may significantly reduce the number of patients that the user needs to review for potential trial eligibility, thereby improving trial recruitment for the practice as the user is spending more time on reviewing patients with a higher likelihood of eligibility.

Computing device 102 may be configured to determine one or more suggested eligible patients for the new trial. For example, computing device 102 may create a patient-trial matching algorithm for determining one or more eligible patients for the new trial based on trial eligibility criteria of the trial. Computing device 102 may also obtain electronic medical records associated with a plurality of patients. For example, computing device 102 may obtain electronic medical records associated with the patients at one or more clinical sites where client device 101 and/or computing device 102 operate from a database (e.g., database 103, database 160). Computing device 102 may further determine one or more eligible patients for the trial based on the electronic medical records and algorithm.

By way of example, the trial eligibility criteria for an example trial may include the following criteria:

1. Is the patient over 18? If yes, go to step 2. If not, they are not eligible.

2. Does the patient have breast cancer? If yes, go to step 3. If not, go to step 4.

3. Is the patient estrogen receptor negative (ER−) and progesterone receptor negative (PR−)? If yes, they are eligible. If not, they are not.

4. Does the patient have colorectal cancer? If yes, go to step 5. If not, they are not eligible.

5. Does the patient have a gene Kirsten rat sarcoma viral oncogene homolog (KRAS) mutation? If yes, they are eligible. If not, they are not.

Figure 4A:
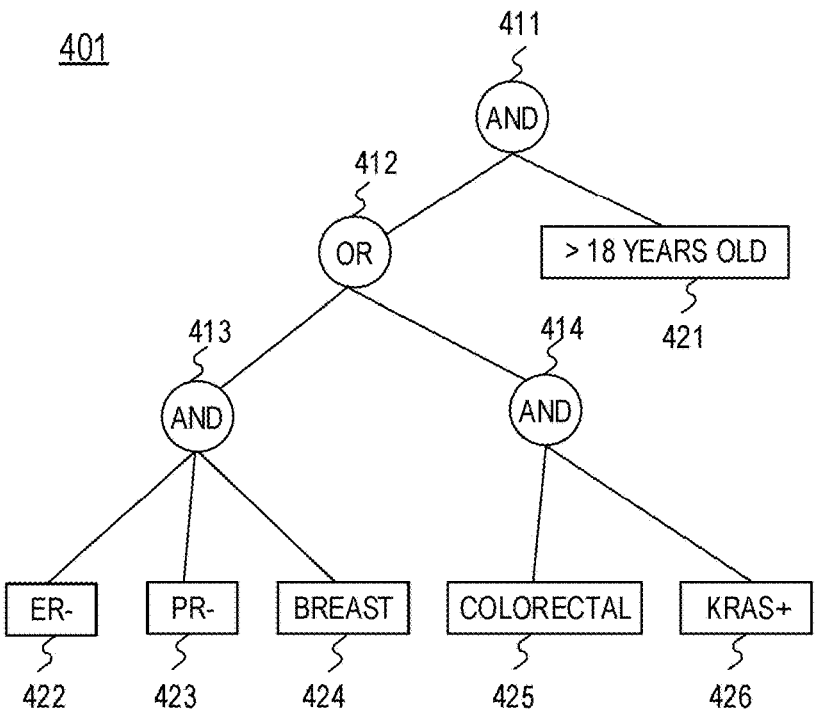
FIGS. 4A and 4B are diagrams illustrating exemplary expression tree structures for one or more suggested patients for a trial, consistent with the present disclosure.

The above trial eligibility criteria may be represented with Boolean operators, as follows:

(Age>18) AND (ER=Negative AND PR=Negative AND Disease=Breast) OR (KRAS=Positive AND Disease=Colorectal), which may be represented as an exemplary expression tree 401 illustrated in FIG. 4A.

As shown in FIG. 4A, expression tree 401 may include operators 411, 412, 413, and 414, and criteria elements 421, 422, 423, 424, 425, and 426. For example, element 412 may represent that the patient must be over 18 years old. As another example, operators 413 and 414, and elements 422-426 represent that the patient must be either (1) ER negative and PR negative and having breast cancer, or (2) having colorectal cancer and KRAS positive. When computing device 102 evaluates each node, computing device 102 may bubble up the result to the node above it and obtain a result of whether a patient is eligible for this trial. For example, for a patient who has breast cancer and is ER– and PR–, but doesn't have colorectal cancer and hasn't tested KRAS+ may be eligible for the trial because of the left subtree of express tree 401.

In some embodiments, each leaf node in the expression tree represents a single inclusion or exclusion criterion. The nodes (and their criteria) may be mixed and matched into different trees to form the criteria for different trials. Each leaf node may have a role in determining whether a patient is eligible, e.g., taking a patient's clinical information as its input and returning a value that may affect the eligibility as an output. Using an expression tree, the system may enable the user to visualize the matching criteria for a trial and may query various data sources (e.g., electronic medical records of the patients) through a unified interface.

Figure 4B:
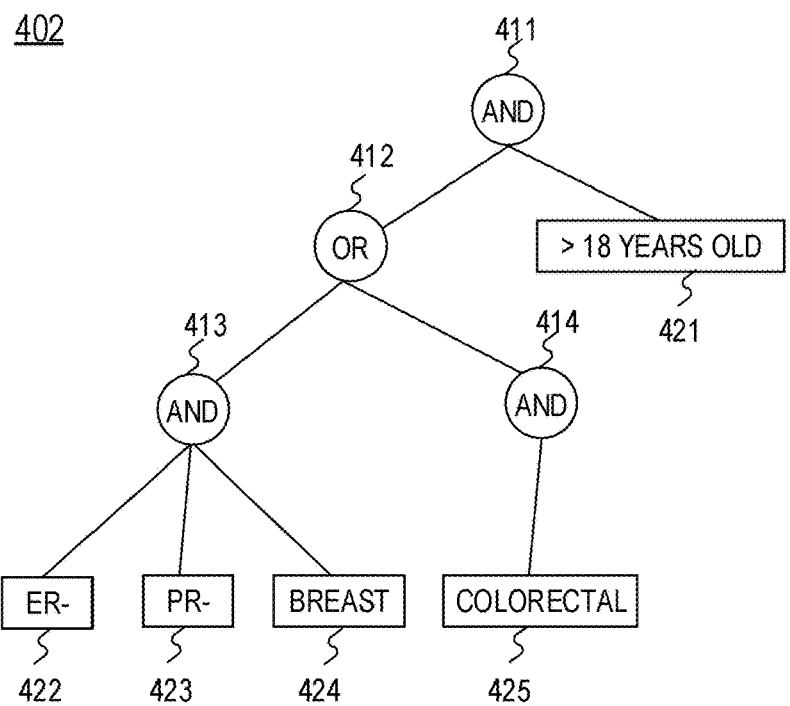

In some embodiments, computing device 102 may be configured to receive updated patient eligibility criteria for the trial. Computing device 102 may also update the patient-trial matching algorithm based on the updated patient eligibility criteria and determine at least one new suggested patient for the updated new trial based on the updated patient-trial matching algorithm and the electronic patient medical records. For example, the user may update the trial eligibility criteria of the trial, and computing device 102 may automatically update the expression tree and patient-trial matching algorithm. As another example, computing device 102 may receive updated trial eligibility criteria from an external database and automatically update the algorithm for the trial based on the updated trial eligibility criteria. By way of example, computing device 102 may receive a user input from the user to delete the KRAS criterium. Computing device 102 may update expression tree 401 by removing leaf node 426 into express tree 402 as illustrated in FIG. 4B. Similarly, if the user adds a new criterium, computing device 102 may insert a new leaf node into the expression tree at an appropriate location. Alternatively or additionally, computing device 102 may modify a leaf node based on input from the user or the system.

Figure 5:
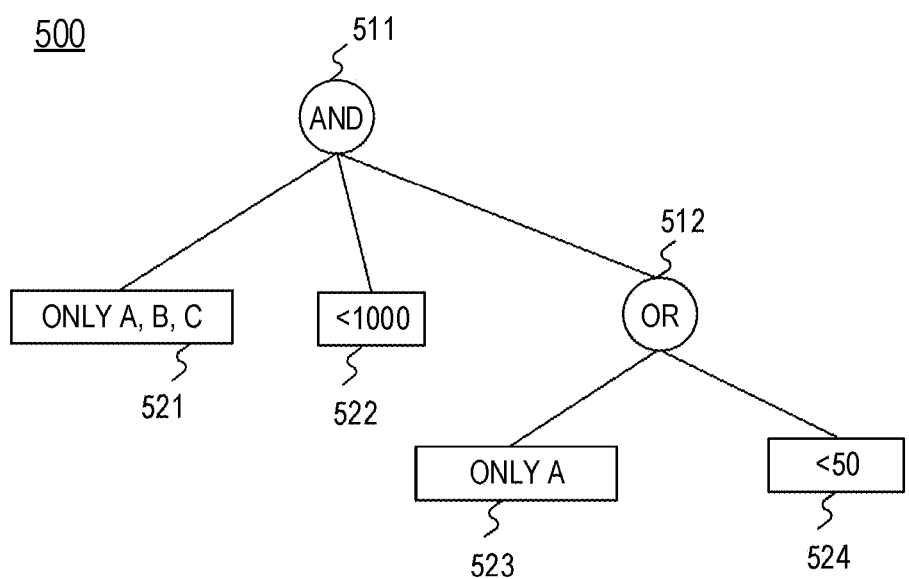
FIG. 5 is a diagram illustrating exemplary expression tree structure for one or more suggested patients for a trial, consistent with the present disclosure.

FIG. 5 is a diagram illustrating an exemplary (simplified) expression tree structure, consistent with the present disclosure. FIG. 5 provides an example to further illustrate an expression tree and algorithm. Expression tree 500 may represent trial eligibility criteria including:

(only A, B, C) AND (<1000) AND (only A OR <50).

Expression tree 500 may include operator nodes 511 and 512, which are two operator classes (AND and OR). Operator classes may include children added as leaf classes (e.g., leaves 521, 522, 523, and 524).

Computing device 102 may automatically generate an algorithm representing expression tree 500 based on the trial eligibility criteria. Exemplary code of the algorithm is shown below.

```
class OrMatchOperator( ):
    def init_(self):
        self.children = [ ]
    def match(self, patient):
        prob_no_match = 1.0
        for child in self.children:
            prob_no_match *= float(1 - child.match(patient))
        return 1 - prob_no_match
class AndMatchOperator( ):
    def init_(self):
        self.children = [ ]
    def match(self, patient):
        prob_match = 1.0
        for child in self.children:
            prob_match *= float(child.match(patient))
        return prob_match
# Mock leaf node that sees whether a MockClass has only certain letters
# in its 'letters' attribute class LetterMatchLeaf( ):
    def init_(self, allowable_letters):
        self.allowable_letters = allowable_letters
    def match(self, patient):
        if set(patient.letters) - set(self.allowable_letters):
            return 0
        return 1
# Mock leaf node that sees whether a MockClass has a number
# less than a max_number class NumberMatchLeaf( ):
    def init_(self, max_number):
        self.max_number = max_number
    def match(self, patient):
        return int(patient.number <= self.max_number)
from collections import namedtuple
MockClass = namedtuple('MockClass', ['number', 'letters'])
tree = AndMatchOperator( )
tree.children.append(LetterMatchLeaf(['A', 'B', 'C']))
tree.children.append(NumberMatchLeaf(1000))
subtree = OrMatchOperator( )
subtree.children.append(NumberMatchLeaf(50))
subtree.children.append(LetterMatchLeaf(['A']))
tree.children.append(subtree)
print('Match! (50, [C])') print(tree.match(MockClass(50, ['C'])))
print('Match! (50, [A])')
print(tree.match(MockClass(55, ['A'])))
print('Fits neither attribute in the subtree. No match. (50, [C])')
print(tree.match(MockClass(55, ['C'])))
print('Number is too big for the top-level number constraint.
No match. (1005, [A])')
print(tree.match(MockClass(1005, ['A'])))
```

The above exemplary code may represent expression tree 500 including the trial eligibility criteria. Computing device 102 may also generate a MockClass for each of the patients, which may be a namedtuple that has a number and a series of letters. For example, computing device 102 may create a namedtuple based on the electronic medical record associated with a patient. The codes also include a leaf class, LetterMatchLeaf, which may only allow a certain subset of letters, and another leaf class, NumberMatchLeaf, which may only allow numbers less than a certain number. One having ordinary skills in the art would understand that these classes are only for illustration purposes and other types of classes may also be used for the algorithm. For example, the algorithm may include a leaf class DiseaseMatchLeaf for disease match and a leaf class BiomarkerMatchLeaf for biomarker match.

Computing device 102 may evaluate different MockClass objects (i.e., the patients) against expression tree 500 using the algorithm, which may return 1 (eligible) or 0 (illegible). In some embodiments, a patient-trial matching algorithm may output a probability, and computing device 102 may determine whether a patient is eligible for the trial based on the probability (e.g., the probability exceeding a threshold).

In some embodiments, computing device 102 may obtain or generate a machine learning algorithm for determining one or more suggested eligible patients for the trial based on the trial eligibility criteria. For example, computing device 102 may obtain a neural network for determining one or more suggested eligible patients for the trial.

Figure 6:
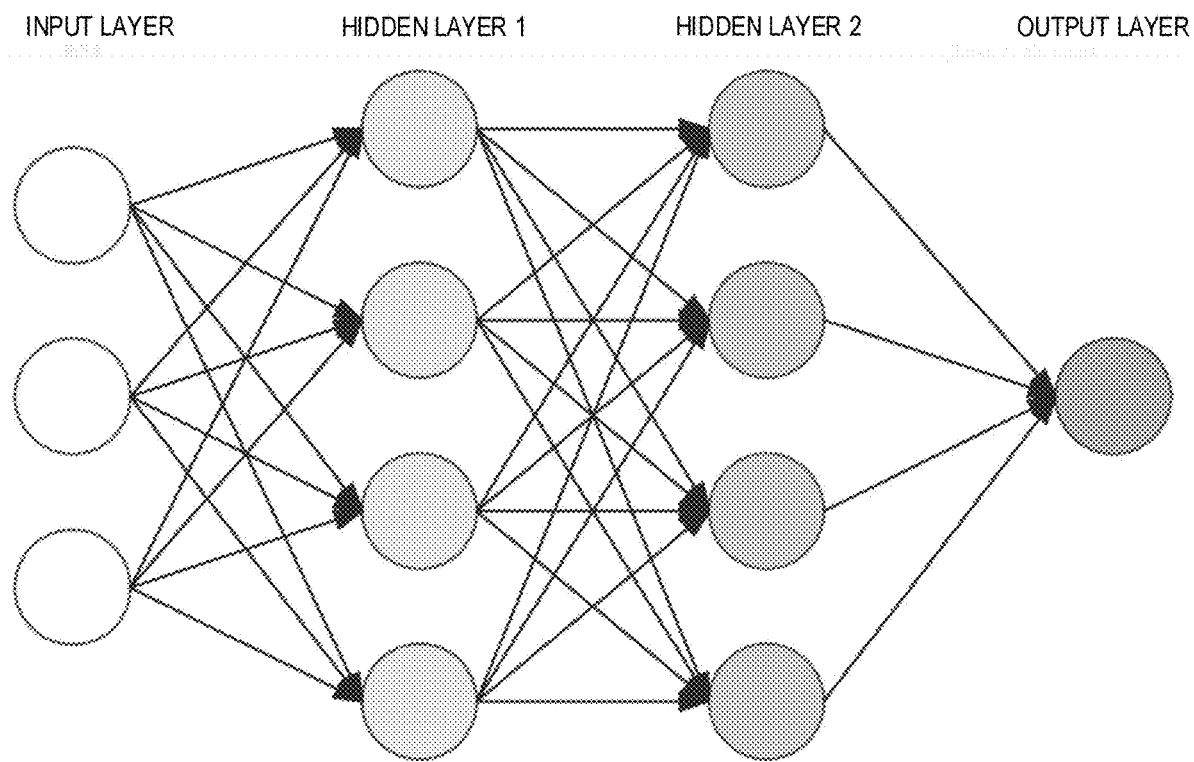
FIG. 6 is a diagram illustrating an exemplary neural network for providing one or more suggested patients for a trial, consistent with the present disclosure.

FIG. 6 illustrates an exemplary neural network 600. Neural network 600 may include an input layer, one or more hidden layers, and an output layer. Each of the layers may include one or more nodes. In some embodiments, the output layer may include one node. Alternatively, the output layer may include a plurality of nodes, and each of the nodes may output data. The input layer may be configured to receive input (e.g., an electronic medical record associated with a patient). In some embodiments, every node in one layer is connected to every other node in the next layer. A node may take the weighted sum of its inputs and pass the weighted sum through a non-linear activation function, the results of which may be output as the input of another node in the next layer. The data may flow from left to right, and the final output may be calculated at the output layer based on the calculation of all the nodes. Neural network 600 may output a probability indicating eligibility of the patient for the trial.

In some embodiments, computing device 102 may determine a patient-trial match between a plurality of patients and a plurality of trials, based on the patient-trial matching algorithms associated with the trials and electronic medical records of the patients. For example, computing device 102 may determine one or more suggested eligible patients for each of the trials and/or one or more suggested eligible trials for each of the patients. Computing device 102 may also generate a data structure representing the relationship between the patients and trials and store the data structure in a database (e.g., database 103, database 160). Computing device 102 may further present the data representing the relationship between the patients and trials to the user. For example, computing device 102 may be configured to generate a patient-trial matching report. By way of example, computing device 102 may receive user input for defining filters for the data to appear on the report, including, for example, patient information (e.g., gender, age, location, patient schedule, diagnosis, biomarker, or the like, or a combination thereof), treatment information (e.g., treatment, inclusionary and/or exclusion drug), and trial information (trial name, study drug, sponsor, study type, trial description, diagnosis, biomarker criteria, line of therapy, or the like, or a combination thereof). Computing device 102 may compile the patients and/or trials that match the filtered data into a report.

FIG. 7 is a diagram illustrating an exemplary graphical user interface for providing one or more suggested trials for patients, consistent with the present disclosure. User interface 700 may be displayed via output device 154 of computing device 102 (e.g., a display or touchscreen), and the user may enter information via input device 153. Alternatively or additionally, computing device 102 may transmit instructions to client device 101 for displaying graphical user interface 700 via an output device of client device 101 (e.g., a display or touchscreen) and for receiving user input via an input device of client device 101.

The user may select a patient schedule, and computing device 102 may access the patient schedule and determine the patients who have been scheduled for a visit according to the patient schedule. For example, the user may select a date (e.g., Nov. 8, 2018 shown in FIG. 700), and computing device 102 may access a patient schedule and determine the patients who have been scheduled for a visit on that date. Alternatively or additionally, the user may view a patient schedule for a period (e.g., a week, a month). Computing device 102 may also provide the user with an interface that shows information relating to the patients and visits. For example, as illustrated in FIG. 7, graphical user interface 700 may include the patients' names, diagnoses, visit types (e.g., office visit, treatment), physicians who the patients visit, locations of the visits, or the like, or a combination thereof.

Computing device 102 may further determine one or more suggested trials for the patients based on the algorithm associated with the trials and the electronic medical records of the patients as described elsewhere in this disclosure. Computing device 102 may also represent graphical user interface 700 to the user, including a list of suggested trials for the patients. As illustrated in FIG. 7, graphical user interface 700 may include a patient list 701, which may include the information of the patients, such as each patient's name, diagnosis, visit type, trial, patient's status, or the like, or a combination thereof. User interface 700 may also include filters 702 configured to receive the user's input to filter patients and/or trials according to, for example, physician, location, patient diagnosis, visit type, trials, patient status, or the like, or a combination thereof. By presenting suggested trials for the patients who have been scheduled for a visit, the patient-trial matching may be tied directly to the patient schedule of the practice (e.g., a clinical) so that the user of the system can identify eligible patients who are visiting the clinical on a particular date and can schedule meetings with these patients to discuss a potential opportunity to participate in the trials. This may improve the patient recruitment. For example, computing device 102 may provide the user with one or more suggested eligible patients who will visit a clinic on a particular date. As another example, the user may filter the trials and/or patients according to diseases, type of trials, or the like, or a combination thereof. Computing device 102 may inform the physician and/or research coordinator to discuss with the patient about the trial in which the patient may be eligible for participation. For example, computing device 102 may include the trial information into the patient's medical record so that the physician may be reminded when discussing with the patient.

In some embodiments, graphical user interface 700 may display a patient schedule including a doctor appointment of at least one suggested patient. Alternatively or additionally, graphical user interface 700 may display information of a doctor or a location associated with the doctor appointment of the patient.

In some embodiments, computing device 102 may update graphical user interface 700 according to the user's input. For example, if a patient name or patient record has been selected (e.g., clicked into), graphical user interface 700 may show that the patient name or patient record appears as "viewed" (e.g., displaying a "viewed" icon by the name of the patient or by another patient identifier). User interface 700 may include a filter to filter the patient(s) who have been viewed.

In some embodiments, graphical user interface 700 may also include different views according to the user's preferences. For example, graphical user interface 700 may include a "Suggested Trials" view, as shown in FIG. 7, which may display the patients with suggested trials actively recruiting or pending trials that match the patient(s)'s diagnosis and biomarkers). Alternatively or additionally, graphical user interface 700 may include a "New Patients" view (not shown), which may display patients who are new to the practice and are having their first visit to the practice. Alternatively or additionally, graphical user interface 700 may include a "Recent Updates" view, which may display patients with suggested trials or who were previously marked as "candidate" or "watching" and should be considered (or reconsidered) now because of a recent scan or pathology report. As another example, recent updates may include a recent scan such as, for example, a pathology or scan report received or a scan order created in the electronic health record associated with a patient since his or her last office visit.

In some embodiments, when the user clicks or selects a patient name in graphical user interface 700, computing device 102 may process the input and provide another graphical user interface for displaying the information of the patient to the user. For example, FIGS. 8A and 8B are diagrams illustrating an exemplary graphical user interface 800 for providing information of a patient and suggested trials, consistent with the present disclosure. User interface 800 may be displayed via output device 154 of computing device 102 (e.g., a display or touchscreen), and the user may enter information via input device 153. Alternatively or additionally, computing device 102 may transmit instructions to client device 101 for displaying graphical user interface 800 via an output device of client device 101 (e.g., a display or touchscreen) and for receiving user input via an input device of client device 101.

As illustrated in FIG. 8A, a user may click or select the patient "Ollie X. Sitedemann" in graphical user interface layout 810 (which is similar to graphical user interface 700). Computing device 102 may provide the user with a graphical user interface layout 820, which may partially overlap with graphical user interface layout 810, for displaying the information of the patient. By way of example, graphical user interface layout 820 may include a region 821 displaying the clinical information of the patient, including, for example, patient's diagnosis information, last office visit, disease, or the like, or a combination thereof. In some embodiments, graphical user interface layout 820 may allow the user to open the electronic medical record of the patient. User interface layout 820 may also include a region 822 displaying one or more suggested and/or existing trials for the patient, which may include the trial information, such as trial name, trial description, trial status, trial disease, trial line of therapy, or the like, or a combination thereof. In some embodiments, graphical user interface 800 may display information associated with two or more trials, which may include the statuses of the trials.

In some embodiments, graphical user interface 800 may present more detailed information regarding a trial. For example, the user may select a trial named "Trial B" in region 822, and computing device 102 may update region 822 of graphical user interface 800 for displaying more information of the trial, as illustrated in FIG. 8B. For example, region 822 may be updated to display a trial timeline of the trial.

In some embodiments, graphical user interface 800 may allow the user to take an action on the information of patient and/or one or more of the trials. For example, graphical user interface 800 may allow the user to update the information (e.g., marking the patient as unviewed). The updated information may be displayed on graphical user interface 800 accordingly. In some embodiments, the updated information may be saved for further use and/or be made available for another user of the system. For example, when a first user has viewed a patient (by, for example, clicking or selecting in graphical user interface 800), computer device 102 may label the patient as "viewed." Computing device 102 may also provide a second user with an graphical user interface including an indicator indicating that this patient has been viewed. Alternatively or additionally, graphical user interface 800 may allow the user to set up a reminder for the user, physician, or research coordinator, or the like, or a combination thereof, to visit the information. By way of example, graphical user interface 800 may allow the user to create a reminder for a physician who has been scheduled to see the patient to look into potentially eligible trials.

Figure 9:
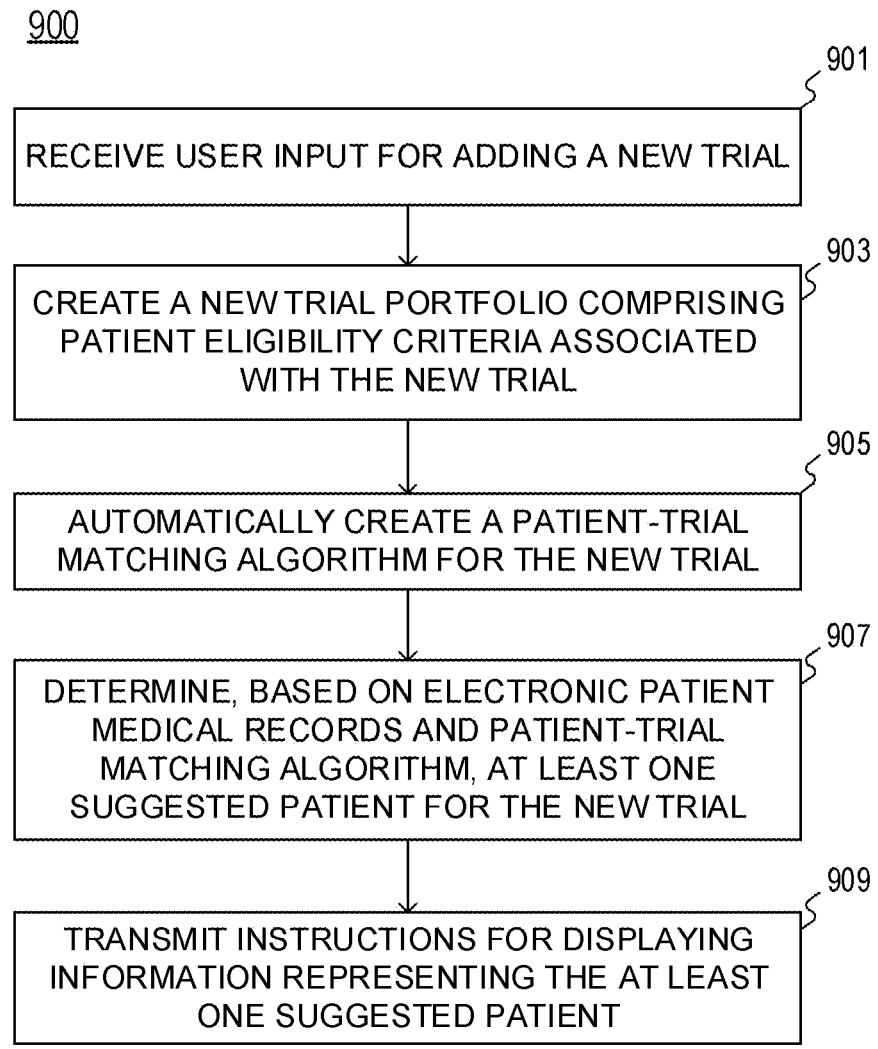
FIG. 9 is a flowchart illustrating an exemplary process for providing one or more suggested patients for a trial, consistent with the present disclosure.

FIG. 9 is a flowchart illustrating an exemplary process 900 for providing one or more suggested patients for a trial, consistent with the present disclosure. While process 900 is described in connection with computing device 102, one skilled in the art would understand that one or more steps of process 900 may be performed by other components of the system (e.g., client device 101 or processor 151).

At step 901, computing device 102 may receive user input via a graphical user interface of computing device 102 or client device 101 for creating a new trial, as described in this disclosure. By way of example, the user may enter an identification number (e.g., an NCT number or ClinicalTrials.gov identifier) at an interface of client device 101 for creating a new trial (e.g., graphical user interface 300 illustrated in FIG. 3). Client device 101 may transmit the identification number to computing device 102. Computing device 102 may obtain trial information from a database (e.g., database 103, database 160) based on the identification number. In some embodiments, the graphical user interface may allow the user to enter trial information in one or more fields, as illustrated in FIG. 3. For example, the user may enter the trial information, such as trial name, study drug, sponsor, study type, trial description, diagnosis, biomarker criteria, line of therapy, or the like, or a combination thereof, via graphical user interface 300.

At step 903, computing device 102 may be configured to create a new trial portfolio based on the user input and/or trial information, as described in this disclosure. In some embodiments, the trial portfolio may include trial eligibility criteria associated with the trial.

At step 905, computing device 102 may be configured to automatically create a patient-trial matching algorithm for determining one or more eligible patients for the new trial based on the trial eligibility criteria, as described elsewhere in this disclosure. For example, computing device 102 may automatically create a patient-trial matching algorithm representing an expression tree (e.g., expression tree 401 illustrated in FIG. 4A) or neutral network (e.g., neural network 600 illustrated in FIG. 6) based on the trial eligibility criteria.

At step 907, computing device 102 may be configured to determine, based on electronic patient medical records associated with a plurality of patients and the patient-trial matching algorithm, at least one suggested patient determined to be eligible for the new trial, as described in this disclosure. For example, computing device 102 may generate a nametuple for each of the patients based on electronic medical records associated with the patient, which may include a number and a series of letters. Computing device 102 may evaluate the nametuples against an expression tree using the algorithm, which may return 1 (eligible) or 0

(illegible). Computing device 102 may determine whether a patient is eligible for the trial based on the returned value by the algorithm.

At step 909, computing device 102 may be configured to transmit, to client device 101 or output device 154, instructions for displaying information representing the at least one suggested patient in the graphical user interface, as described in this disclosure. For example, computing device 102 may transmit to client device 101 instructions for displaying graphical user interfaces 700 and 800 illustrated in FIGS. 7, 8A, and 8B.

FIG. 10 illustrates an exemplary graphical user interface for displaying and modifying trial information for a patient, consistent with the present disclosure. Computing device 102 may provide a user (e.g., a trial research coordinator, a physician, a medical personnel, etc.) graphical user interface 1000 for displaying trial information for a patient. User interface 1000 may be displayed via output device 154 of computing device 102 (e.g., a display or touchscreen), and the user may enter information via input device 153. Alternatively or additionally, computing device 102 may transmit instructions to client device 101 for displaying graphical user interface 1000 via an output device of client device 101 (e.g., a display or touchscreen) and for receiving user input via an input device of client device 101.

Computing device 102 may determine a potentially eligible trial, e.g., "Trial B," for a patient, as described elsewhere in this disclosure. Computing device 102 may provide graphical user interface 1000 to the user, which may include the information associated with the Trial B trial to the user. The information associated with the trial may include such as a trial name, trial description, trial status, trial disease, trial line of therapy, or the like, or a combination thereof. User interface 1000 may also include the information relating to the patient (e.g., gender, age, location, patient schedule, diagnosis, biomarker, drug order history, or the like, or a combination thereof). In some embodiments, graphical user interface 1000 may further include a control (e.g., a button, a link, a box, etc.) for opening the electronic medical record of the patient.

In some embodiments, graphical user interface 1000 may be configured to receive user input from the user to update the status of the trial for the patient. For example, graphical user interface 1000 may be configured to receive user input to modify the status of the trial for the patient to "In Pre-screening," which may indicate that the patient could be considered as a candidate for the trial. Computing device 102 may be configured to update the status of the trial for the patient based on the received user input. Computing device 102 may also be configured to obtain and/or generate information relating to the update and associate the information with the update. For example, computing device 102 may obtain and/or generate information relating to the user who updates the status of the trial (e.g., the user's name, ID, profession, association, etc.), information relating to the update (e.g., the time and/or date when the update occurs), information relating to the patient, or the like, or a combination thereof.

In some embodiments, graphical user interface 1000 may also be configured to receive user input for entering information relating to the status update. For example, graphical user interface 1000 may be configured to receive user input for entering the date of the status change (e.g., by receiving a selection of a date indicating "When did you begin pre-screening the patient?" as illustrated in FIG. 10). User interface 1000 may also be configured to receive user input for entering comments relating to the status change from the user.

In some embodiments, graphical user interface 1000 may be a graphical user interface layout overlapping with another graphical user interface layout (e.g., graphical user interface 700 illustrated in FIG. 7, graphical user interface layout 810 illustrated in FIGS. 8A and 8B). For example, as illustrated in FIG. 7, graphical user interface 700 may include a patient list 701, which may include the information of the patients, such as each patient's name, diagnosis, visit type, trial, patient's status, or the like, or a combination thereof. The user may select one or more patients listed in patient list 701, and graphical user interface 1000 may be displayed to the user via output device 154 of computing device 102. User interface 1000 may include the trial information and the patient information as described elsewhere in this disclosure.

In some embodiments, computing device 102 may update an electronic medical record associated with the patient if the patient information, trial information, and/or treatment information has been updated. For example, a first user (e.g., a research coordinator) may update the trial information relating to a patient via graphical user interface 1000 (e.g., adding a potentially eligible trial to the patient), and computing device 102 may update the electronic medical record associated with the patient. Computing device 102 may also be configured to display updated electronic medical record to other users (e.g., a physician associated with the patient). In some embodiments, computing device 102 may send a notification for the updates associated with the patient to relevant personnel. For example, computing device 102 may send a notification to a physician of the patient if the patient is potentially eligible for a trial as determined according to the process as described elsewhere in this disclosure.

FIGS. 11A-11F are diagrams illustrating exemplary graphical user interface 1100 for displaying and modifying trial information for a patient, consistent with the present disclosure. User interface 1100 may be displayed via output device 154 of computing device 102 (e.g., a display or touchscreen), and a user may enter information via input device 153. Alternatively or additionally, computing device 102 may transmit instructions to client device 101 for displaying graphical user interface 1100 via an output device of client device 101 (e.g., a display or touchscreen) and for receiving user input via an input device of client device 101.

In some embodiments, the information presented in graphical user interface 1100 may be generated and/or updated according to updated electronic medical record associated with the patient. For example, graphical user interface 1100 may present information to a physician associated with the patient after a research coordinator updates the trial information relating to the patient via, for example, graphical user interface 1000, as described elsewhere in this disclosure.

As illustrated in FIG. 11A, graphical user interface 1100 may include a first area 1110 configured to display patient information. Patient information may include the gender, age, location, patient schedule, diagnosis, biomarker, examination room, or the like, or a combination thereof. In some embodiments, graphical user interface 1100 may include a second area 1120 configured to display treatment information. Treatment information may include the treatment plan, inclusionary and/or exclusion drug, treatment schedule, change history, or the like, or a combination thereof.

In some embodiments, graphical user interface 1100 may also include one or more indicators 1131, 1132, and 1133 that include information specifying that the patient is potentially eligible for one or more trials, the patient is participating in one or more trials, or the patient has entered a follow-up stage for one or more trials (and/or needs a follow-up evaluation or study for one or more trials). For example, indicator 1131 may indicate that the patient has one or more trials that she is participating, indicator 1132 may indicate that the patient has one or more potentially eligible trials, and indicator 1133 may indicate that the patient has entered a follow-up stage for one or more trials.

In some embodiments, one or more indicators 1131, 1132, and 1133 may be displayed in association with the name of the patient. For example, the indicator may include text displayed next to the patient name in the graphical user interface. By way of example, indicator 1131 may include words "on study," indicator 1132 may include words "potential trials," and indicator 1133 may include words "in follow up." Indicator 1131 having words "on study" may indicate that the patient is actively enrolled in one or more trials. Indicator 1132 having words "potential trials" may indicate there are potential trial treatment options for the patient. Indicator 1133 having words "in follow up" may indicate that the patient is no longer active on one or more trials, but is being followed up for safety surveillance, data collection, or other reasons (or the patient has been entered a follow-up stage for one or more trials).

In some embodiments, indicators 1131, 1132, and/or 1133 may include information relating the number of the trial(s) associated with the indicators. For example, indicator 1132 may include the words "potential trials" are displayed next to the patient name and the number "2" (i.e., the number of potential trials for consideration for the patient) is displayed after the words "potential trials."

In some embodiments, indicators 1131, 1132, and/or 1133 may include at least one of text, a shape, a color, or an image. Alternatively or additionally, indicators 1131, 1132, and/or 1133 may include text surrounding by a shape.

In some embodiments, graphical user interface 1100 may be configured to receive user input from a user and display additional information based on the received user input. The additional information may include the patient information, the treatment information, the trial information, or the like, or a combination thereof. The trial information may also include trial name, research coordinator, study drug, sponsor, study type, trial description, diagnosis, biomarker criteria, line of therapy, or the like, or a combination thereof.

Figure 11B:
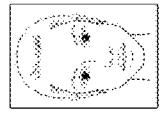

For example, the user may interact with one or more indicators 1131, 1132, and/or 1133 by clicking an indicator (or a link or area associated with the indicator). By way of example, graphical user interface 1100 may include indicator 1133, which may include information specifying that the patient has entered a follow-up stage for one or more trials. The user may select indicator 1133 via graphical user interface 1100 (e.g., by clicking indicator 1133), and graphical user interface 1100 may display the trial information relating to the one or more trials for which the patient has entered a follow-up stage. For example, as illustrated in FIG. 11B, graphical user interface 1100 may display a pop-up window 1143, which may include the trial information relating to a trial named "NATE12071."

Alternatively or additionally, the user may select indicator 1132 via graphical user interface 1100 (e.g., by clicking indicator 1132), and graphical user interface 1100 may display the trial information relating to the one or more trials for which the patient is potentially eligible. By way of example, as illustrated in FIG. 11C, graphical user interface 1100 may display a pop-up window 1142, which includes the trial information relating to the one or more trials for which the patient is potentially eligible. The trial information may include trial name, research coordinator, study drug, sponsor, study type, trial description, diagnosis, biomarker criteria, line of therapy, or the like, or a combination thereof.

Figure 11D:
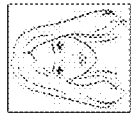

In some embodiments, graphical user interface 1100 may be configured to receive user input from the user for modifying the trial information relating to one or more trials and the patient. For example, the trial information displayed in graphical user interface 1100 may include a selectable action, which may include at least a first option to designate the patient for consideration for the at least one trial and a second option to designate the patient to not be considered for the at least one trial. For example, as illustrated in FIG. 11C, pop-up window 1142 may include a selectable physician action for trials Trial B and Trial C, which may include a first option (labeled "Do not consider") to designate the patient for consideration for one or more of the trials. The selectable physician action may also include a second option (labeled "Consider") to designate the patient to not be considered for one or more of the trials. User interface 1100 may also be configured to receive user input from the user for interacting with the selectable action. For example, graphical user interface 1100 may receive the user input from the user to select the second option (labeled "Consider") for trial Trial C to designate the patient to be considered for trial Trial C. As another example, graphical user interface 1100 may receive the user input from the user to select the first option (labeled "Do not consider") for trial Trial B to designate the patient not to be considered for trial Trial B. In some embodiments, graphical user interface 1100 may display a notification indicating that the user has selected the first or second option for a trial. For example, as illustrated in FIG. 11D, graphical user interface 1100 may display a notification 1152 when the user selects the second option for trial Trial B to designate the patient not to be considered for trial Trial B.

In some embodiments, graphical user interface 1100 may also be configured to receive user input from the user to specify the reason why the user selects the first option or the second option. For example, as illustrated in FIG. 11E, pop-up window 1142 in graphical user interface 1100 may display one or more selectable reasons specifying why the patient should not be considered for trial Trial B. By way of example, the plurality of selectable reasons specifying why the patient should not be considered for the at least one trial may include at least a first reason indicating that the patient does not want to be in a clinical trial, a second reason indicating that the patient has a poor performance status, a third reason indicating that treatment is not indicated, and a fourth reason specifiable by the user.

Figure 11F:
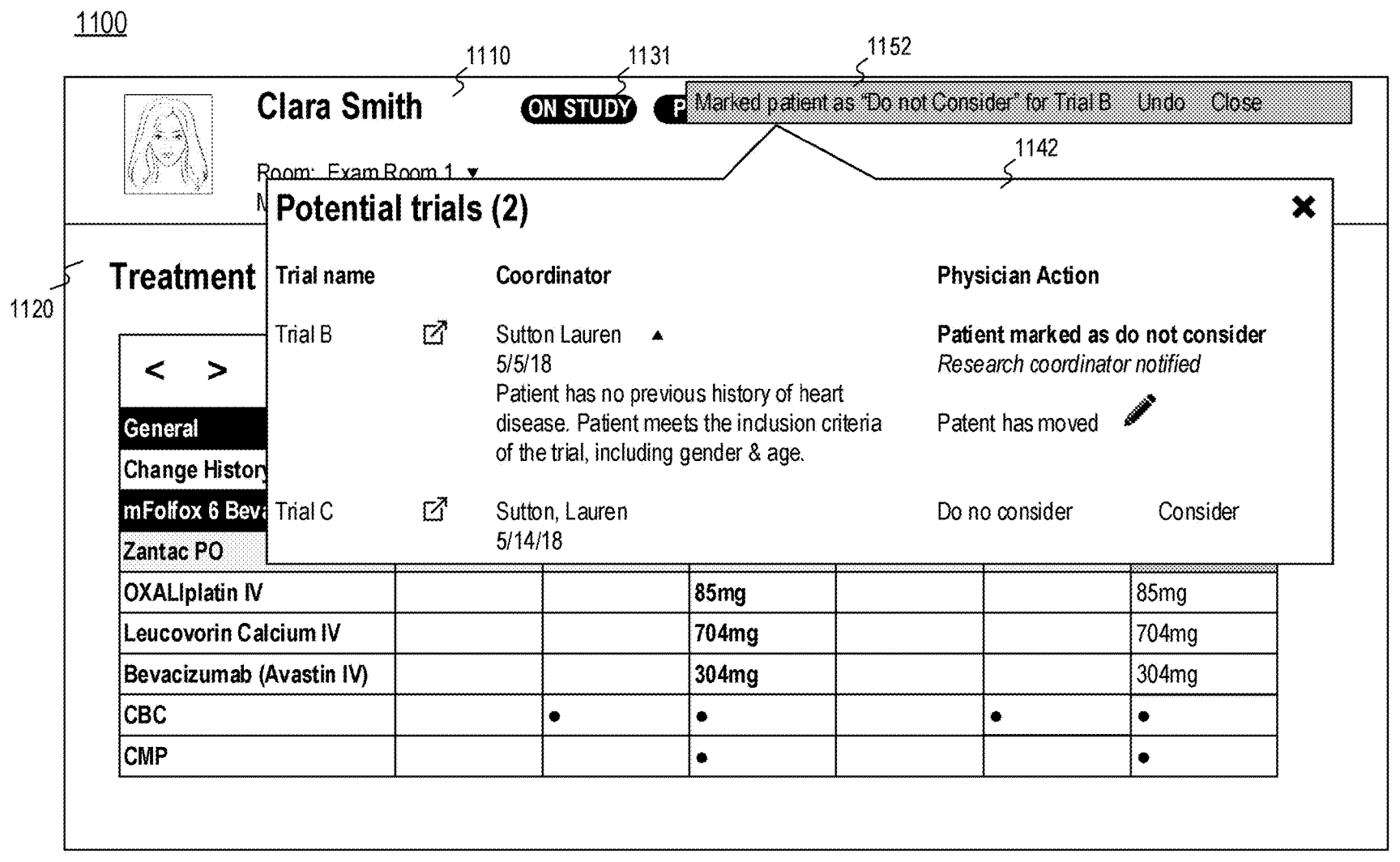

In some embodiments, graphical user interface 1100 may be configured to receive user input from the user to enter text information relating to the reason. For example, as illustrated in FIG. 11F, the user may enter the text "Patient has moved" as the reason why the patient should not be considered for trial Trial B via, for example, graphical user interface 1100.

In some embodiments, computing device 102 may update the electronic medical record and/or trial information associated with the patient and the trial(s) for which trial information has been updated. Alternatively or additionally, computing device 102 may send updated information (patient information, trial information, etc.) to relevant personnel. For example, computing device 102 may update the electronic medical record including the information that the patient will not be considered for trial Trial B. Other users (e.g., a physician, research coordinator, etc.) may view the most recent information relating to the patient and/or trial.

In some embodiments, graphical user interface 1100 may be configured to display one or more indicators and trial information associated with one or more trials based on the trial information, patient information, or the like, or a combination thereof. For example, graphical user interface 1100 may sort or filter the trials to be displayed according to a physician, clinic location, MRN number, diagnoses, visit type, trial, current status of a trial, sponsor of a trial or the like, or a combination thereof. By way of example, graphical user interface 1100 may display an indicator for one or more trials sponsored by a particular sponsor. Alternatively or additionally, graphical user interface 110 may rank one or more trials sponsored by a particular sponsor higher than other trial(s) (by, for example, placing the trial(s) sponsored by the sponsor on the top of the list of the trials).

In some embodiments, user interface 1100 may be configured to receive user input from the user to explore one or more details regarding a trial. For example, the user may click a trial (or an indicator associated with the trial). User interface 1100 may be configured to open a clinicaltrials.gov webpage associated with the trial, by, for example, opening a separate tab (or a browser) to access the clinicaltrials.gov webpage. This may enable the user to access the trial eligibility criteria from the website to determine whether or not the patient is eligible for the trial.

In some embodiments, computing device 102 may send the updated information associated with a trial to a research coordinator of the trial. FIG. 12 is a diagram illustrating an exemplary graphical user interface 1200 for displaying one or more notifications relating to updates on trial information of a patient, consistent with the present disclosure. User interface 1200 may be displayed via output device 154 of computing device 102 (e.g., a display or touchscreen), and the user may enter information via input device 153. Alternatively or additionally, computing device 102 may transmit instructions to client device 101 for displaying graphical user interface 1200 via an output device of client device 101 (e.g., a display or touchscreen) and for receiving user input via an input device of client device 101.

For example, as described elsewhere in this disclosure, computing device 102 may update the trial information relating to the patient for trials Trial C and Trial B. Computing device 102 may also be configured to send a research coordinator one or more notifications indicating that the trial information associated with the trial and the patient has been updated. For example, as illustrated in FIG. 12, computing device 102 may provide the research coordinator with graphical user interface 1200, which may include a notification relating to the patient for trial Trial C indicating that the patient has been designated to be considered for the trial. User interface 1200 may also include a notification relating to the patient for trial Trial B indicating the patient has been designated not to be considered for trial Trial B. Potential benefits of updating trial information and sending the updates back to a research coordinator may include increasing the number of patients participating in clinical trials. Additionally, the disclosed systems and methods may enable the integration of the workflows of a research coordinator and a physician, which may enable seamless communication between the research teams reviewing patients for trial eligibility and health care providers responsible for confirming eligibility.

FIGS. 13A-13C are diagrams illustrating exemplary graphical user interfaces for displaying one or more trials, consistent with the present disclosure. User interface 1300 may be displayed via output device 154 of computing device 102 (e.g., a display or touchscreen), and the user may enter information via input device 153. Alternatively or additionally, computing device 102 may transmit instructions to client device 101 for displaying graphical user interface 1300 via an output device of client device 101 (e.g., a display or touchscreen) and for receiving user input via an input device of client device 101.

A user may select a patient schedule, and computing device 102 may access the patient schedule and determine one or more patients who have been scheduled for a visit according to the patient schedule. For example, the user may select a date (e.g., Jul. 1, 2018 shown in FIG. 13A), and computing device 102 may access a patient schedule and determine the patients who have been scheduled for a visit on that date. Alternatively or additionally, the user may view a patient schedule for a period (e.g., a week, a month). Computing device 102 may also provide the user with graphical user interface 1300 (which may be similar to graphical user interface 700 illustrated in FIG. 7) that shows information relating to the patients and visits. For example, as illustrated in FIG. 13A, graphical user interface 1300 may include the patients' names, diagnoses, visit types (e.g., office visit, treatment), physicians who the patients visit, locations of the visits, current status on the trials relating to the patients, or the like, or a combination thereof. In some embodiments, the current status of the trials may include trial information relating to the trials, which may include trial description, trial status, trial disease, trial line of therapy, or the like, or a combination thereof.

In some embodiments, graphical user interface 1300 may be configured to receive user input from the user to sort or filter the trials to be displayed. For example, the user may filter trials according to physician, clinic location, MRN number, diagnoses, visit type, trial, current status of a trial, sponsor of a trial or the like, or a combination thereof. By way of example, the user may select a particular sponsor (e.g., Sponsor1 illustrated in FIG. 13B) via graphical user interface 1300, and graphical user interface 1300 may display the patients associated with the trial(s) sponsored by Sponsor1 (e.g., trial named "Trial D" as illustrated in FIG. 13B). As another example, the user may select Sponsor2 via graphical user interface 1300, and graphical user interface 1300 may display the patients associated with the trial(s) sponsored by Sponsor2 (e.g., trial named "Trial A" as illustrated in FIG. 13C).

Figure 14:
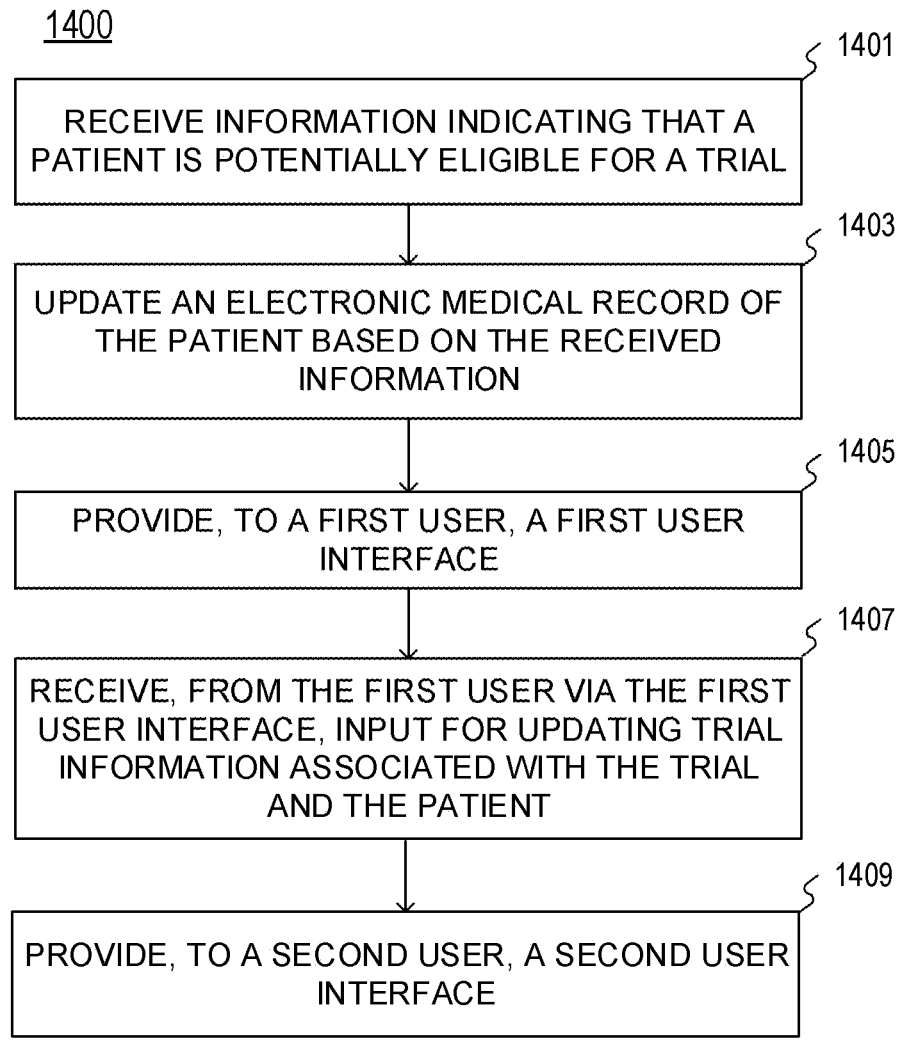
FIG. 14 is a flowchart illustrating an exemplary process for providing graphical user interfaces for updating trial information, consistent with the present disclosure.

FIG. 14 is a flowchart illustrating an exemplary process 1400 for providing graphical user interfaces for updating trial information, consistent with the present disclosure. Process 1400 may be performed by one or more of client devices 101-1 to 101-3 and computing device 102.

At step 1401, computing device 102 may be configured to receive information indicating that a patient is potentially eligible for a trial. The information indicating that the patient is potentially eligible for the trial may be determined according to the method as described elsewhere in this disclosure. For example, computing device 102 may determine that a patient is potentially eligible for a trial based on process 900 as described elsewhere in this disclosure. By way of example, computing device 102 may determine that a patient is potentially eligible for a trial based on the electronic patient medical record associated with the patient and a patient-trial matching algorithm. Alternatively or additionally, computing device 102 may be configured to receive the information from a user (e.g., a research coordinator, physician, or the like, or a combination thereof). By way of example, computing device 102 may be configured to receive the information from a research coordinator via graphical user interface 1000 as described elsewhere in this disclosure (through, for example client device 101-1).

At step 1403, computing device 102 may be configured to update an electronic medical record of the patient based on the received information. For example, an electronic medical record of the patient may include trial information, and computing device 102 may update the trial information associated with the patient. By way of example, computing device 102 may update the trial information associated with the patient to indicate that the patient is potentially eligible for a trial.

In some embodiments, computing device 102 may be configured to provide a notification to relevant personnel based on the received information. For example, computing device 102 may be configured to send a notification to a physician of the patient if the patient is potentially eligible for a trial as determined according to the process as described elsewhere in this disclosure.

At step 1405, computing device 102 may be configured to provide a graphical user interface to a user including an indicator indicating that the patient is potentially eligible for the trial. By way of example, computing device 102 may provide a graphical user interface to a physician associated with the patient through client device 101-2.

In some embodiments, the graphical user interface provided to the user may include graphical user interface 1100 illustrated in FIGS. 11A-11F and described elsewhere in this disclosure. For example, computing device 102 may provide graphical user interface 1100 to the user, which may include an indicator 1132 indicating that the patient has one or more potentially eligible trials. In some embodiments, indicator 1132 indicating that the patient is potentially eligible for the trial may include text displayed next to a name of the patient.

At step 1407, computing device 102 may be configured to receive, from the user via the graphical user interface, input for updating trial information associated with the trial and the patient. The updated trial information may include information indicating whether the patient is being considered for participation in the trial. For example, computing device 102 may be configured to receive from the user a selection of an indicator indicating that the patient is potentially eligible for the trial, and the graphical user interface may display a pop-up window configured to receive input for updating trial information associated with the trial and/or the patient. For example, as illustrated in FIG. 11, graphical user interface 1100 may display a pop-up window 1142, which includes trial information relating to the one or more trials for which the patient is potentially eligible. The trial information may include trial name, research coordinator, study drug, sponsor, study type, trial description, diagnosis, biomarker criteria, line of therapy, or the like, or a combination thereof. Pop-up window 1142 may include a selectable physician action for trials Trial B and Trial C, which may include a first option (labeled "Do not consider") to designate the patient for consideration for one or more of the trials.

At step 1409, computing device 102 may be configured to provide, to a second user, a second graphical user interface, wherein the second graphical user interface comprises at least portion of the updated trial information associated with the trial and the patient. For example, computing device 102 may provide a research coordinator with graphical user interface 1200 including at least portion of the updated trial information associated with trials Trial B and Trial C. By way of example, computing device 102 may provide the research coordinator with graphical user interface 1200 through client device 101-1. In some embodiments, computing device 102 may send one or more notifications to the second user indicating that the trial information relating to a trial and/or patient has been updated.

In some embodiments, computing device 102 may be configured to receive information indicating that the patient is potentially eligible for a plurality of trials. The information indicating that the patient is potentially eligible for a plurality of trials may be determined as described elsewhere in this disclosure. Computing device 102 may also be configured to select at least one of the plurality of trials based on status information associated with the at least one of the plurality of trials. The status information associated with a trial may include a physician, clinic location, MRN number, diagnoses, visit type, trial, current status of a trial, sponsor of a trial or the like, or a combination thereof. For example, computing device 102 may select at least one of the plurality of trials based on a particular sponsor. Computing device 102 may further be configured to provide, to a user, a graphical user interface, which may include an indicator indicating that the patient is potentially eligible for the at least one of the plurality of trials.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for managing electronic medical records, the system including at least one processor programmed to:

access an electronic medical record associated with a patient and trial eligibility criteria associated with at least one trial;

identify, based on the electronic medical record, a plurality of trials the patient is potentially eligible for, wherein identifying the plurality of trials includes:
automatically generating an algorithm representing an expression tree based on the trial eligibility criteria;
generating at least one namedtupule based on the electronic medical record;
evaluating the at least one namedtupule against the algorithm to determine a probability the patient is eligible for the plurality of trials; and
comparing the determined probability to a threshold probability;

determine a ranking of the plurality of trials based on one or more sponsors of the plurality of trials;

cause display of a graphical user interface for displaying the electronic medical record, the graphical user interface comprising:
a first area displaying patient information, the patient information including at least a name of the patient; and
first, second, and third indicators displayed in association with the name of the patient, the first indicator specifying that the patient is potentially eligible for the plurality of trials based on the determined probability, the second indicator specifying a number of trials that the patient is participating in, and the third indicator specifying a number of trials the patient has completed;

wherein, in response to an interaction by a user with the first indicator, the graphical user interface displays a second area, the second area including:
an overlay area that displays a list of the plurality of trials according to the ranking, wherein trials sponsored by a particular sponsor of the one or more sponsors are placed at a top of the list of the plurality of trials;
a selectable action including at least a first option to designate the patient for consideration for one or more of the plurality of trials and a second option to designate the patient to not be considered for one or more of the plurality of trials; and
a selection region for specifying a reason why the patient should not be considered for the plurality of trials, the selection region including a plurality of selectable predefined reasons and at least one reason specifiable by the user, the selection region being displayed based on a selection of the second option by the user;

wherein, in response to an interaction by the user with the second indicator, the graphical user interface displays a third area including trial information associated with the trials that the patient is participating in; and wherein, in response to an interaction by the user with the third indicator, the graphical user interface displays a fourth area including trial information relating to the trials the patient has completed; and update the electronic medical record to indicate the patient should not be considered for the plurality of trials based on the at least one specifiable reason by the user.

2. The system of claim 1, wherein the first indicator includes text displayed next to the patient name in the graphical user interface.

3. The system of claim 2, wherein the text displayed next to the patient name includes words "potential trials," "on study," or "in follow-up".

4. The system of claim 3, wherein when the words "potential trials" are displayed next to the patient name, and a number of the plurality of trials is displayed after the words "potential trials".

5. The system of claim 1, wherein the graphical user interface displays trial information relating to the plurality of trials for which the patient is potentially eligible.

6. The system of claim 5, wherein the trial information relating to the plurality of trials for which the patient is potentially eligible includes a name of at least one trial.

7. The system of claim 5, wherein the trial information relating to the plurality of trials for which the patient is potentially eligible includes a name of a coordinator of at least one trial.

8. The system of claim 1, wherein the plurality of selectable predefined reasons include at least a first reason indicating that the patient does not want to be in a clinical trial, a second reason indicating that the patient has a poor performance status, and a third reason indicating that treatment is not indicated.

9. The system of claim 1, wherein the first, second, and third indicators include at least one of text, a shape, a color, or an image.

10. The system of claim 1, wherein the first, second, and third indicators include text surrounded by a shape.

11. A system for managing electronic medical records, the system comprising:
at least one processor programmed to:
receive information indicating that a patient is potentially eligible for a trial, the information indicating that the patient is potentially eligible for the trial being determined based on a comparison of a probability the patient is eligible for the plurality of trials to a probability threshold, the probability the patient is eligible for the plurality of trials being determined based on evaluating at least one namedtupule against an algorithm, automatically generated by the processor and representing an expression tree based on trial eligibility criteria associated with the plurality of trials;
determine a ranking of the plurality of trials based on one or more sponsors of the plurality of trials;
update an electronic medical record of the patient based on the received information;
provide, to a first user, a first user interface, wherein the first user interface comprises first, second, and third indicators displayed in association with the name of the patient, the first indicator indicating that the patient is potentially eligible for the trial based on the determined probability, the second indicator specifying a number of trials that the patient is participating in, and the third indicator specifying a number of trials the patient has completed, wherein, in response to an interaction by the user with the second indicator, the graphical user interface displays a third area including trial information associated with the trials that the patient is participating in, and wherein, in response to an interaction by the user with the third indicator, the graphical user interface displays a fourth area including trial information relating to the trials the patient has completed;
receive, from the first user via an interaction with the first indicator, input for updating trial information associated with the trial and the patient, wherein the updated trial information comprises information indicating whether the patient is being considered for participation in the trial and, when the patient is not considered for participation in the trial, a reason why the patient is not being considered, the reason why being specified through a selection by the user from one of a plurality of selectable predefined reasons or at least one reason specifiable by the user, the plurality of selectable predefined reasons being displayed in response to an indication by the first user that the patient is not being considered;

update the medical record to indicate the patient should not be considered for the plurality of trials based on the at least one specifiable reason by the user; and provide, to a second user, a second user interface, wherein the second user interface comprises at least portion of the updated trial information associated with the trial and the patient.

12. The system of claim 11, wherein the first indicator includes text displayed next to a name of the patient.

13. The system of claim 11, wherein the at least one processor is further programmed to provide a notification to the first user indicating that the patient is potentially eligible for the trial.

14. The system of claim 13, after receiving input from the first user selecting the first indicator, the first user interface displays a pop-up window for receiving the input for updating trial information associated with the trial and the patient.

15. The system of claim 11, wherein the at least one processor is further programmed to provide a notification to the second user indicating that the trial information associated with the trial and the patient has been updated.

16. The system of claim 11, wherein the at least one processor is further programmed to:

receive information indicating that the patient is potentially eligible for the plurality of trials;

select at least one of the plurality of trials based on status information associated with the at least one of the plurality of trials; and provide, to the first user, a third user interface, wherein the third user interface comprises an indicator indicating that the patient is potentially eligible for the at least one of the plurality of trials.

17. A computer-implemented method for managing electronic medical records, the method comprising:

receiving information indicating that a patient is potentially eligible for a trial, the information indicating that the patient is potentially eligible for the trial being determined based on a comparison of a probability the patient is eligible for the plurality of trials to a probability threshold, the probability the patient is eligible for the plurality of trials being determined based on evaluating at least one namedtupule against an algorithm automatically generated and representing an expression tree based on trial eligibility criteria associated with the plurality of trials ;

determining a ranking of the plurality of trials based on one or more sponsors of the plurality of trials;

updating, by at least one processor, an electronic medical record of the patient based on the received information;

providing, by the at least one processor, a first user interface to a first user, wherein the first user interface comprises first, second, and third indicators displayed in association with the name of the patient, the first indicator indicating that the patient is potentially eligible for the trial based on the determined probability, the second indicator specifying a number of trials that the patient is participating in, and the third indicator specifying a number of trials the patient has completed, wherein, in response to an interaction by the user with the second indicator, the graphical user interface displays a third area including trial information associated with the trials that the patient is participating in, and wherein, in response to an interaction by the user with the third indicator, the graphical user interface displays a fourth area including trial information relating to the trials the patient has completed;

receiving, from the first user via an interaction with the first indicator, input for updating trial information associated with the trial and the patient, wherein the updated trial information comprises an indicator indicating whether the patient is being considered for participation in the trial and, when the patient is not considered for participation in the trial, a reason why the patient is not being considered, the reason why being specified through a selection by the user from one of a plurality of selectable predefined reasons or at least one reason specifiable by the user, the plurality of selectable predefined reasons being displayed in response to an indication by the first user that the patient is not being considered;

updating the medical record to indicate the patient should not be considered for the plurality of trials based on the at least one specifiable reason by the user; and providing, by the at least one processor, a second user interface to a second user, wherein the second user interface comprises at least portion of the updated trial information associated with the trial and the patient.

18. The method of claim 17, further comprising providing a notification to the first user indicating that the patient is potentially eligible for the trial.

19. The method of claim 17, wherein the first indicator includes text displayed next to a name of the patient.

* * * * *